United States Patent
Nadolsky

(10) Patent No.: US 6,492,455 B1
(45) Date of Patent: Dec. 10, 2002

(54) REACTION PRODUCTS OF $C_6+$ ALPHA-OLEFIN/MALEIC ANHYDRIDE COPOLYMERS AND POLYFUNCTIONALIZED AMINES

(75) Inventor: Richard J. Nadolsky, Houston, TX (US)

(73) Assignee: Baker Hughes Incorporated, Houston, TX (US)

( * ) Notice: Subject to any disclaimer, the term of this patent is extended or adjusted under 35 U.S.C. 154(b) by 0 days.

(21) Appl. No.: 09/227,394

(22) Filed: Jan. 8, 1999

Related U.S. Application Data

(60) Provisional application No. 60/070,870, filed on Jan. 9, 1998.

(51) Int. Cl.[7] ............................................... C08L 31/00
(52) U.S. Cl. ..................................... 524/559; 525/327.6
(58) Field of Search ........................ 525/327.6; 524/559

(56) References Cited

U.S. PATENT DOCUMENTS 5,298,568 A  * 3/1994 Suzuki .................... 525/327.6

FOREIGN PATENT DOCUMENTS

| DE | 3328739 A1 | 8/1983 |
|---|---|---|
| DE | 247456 A1 | 4/1986 |
| EP | 0023084 A1 | 1/1981 |
| EP | 0357215 A1 | 3/1990 |
| EP | 0561722 A1 | 10/1996 |
| FR | 2656321 A1 | 12/1989 |

OTHER PUBLICATIONS

Controlling Emulsion Particle Architecture, Jun. 1996, pp. 48–50, 52, 54, *Paint & Coatings Industry*.

* cited by examiner

*Primary Examiner*—Peter D. Mulcahy
(74) *Attorney, Agent, or Firm*—Locke Liddell & Sapp LLP

(57) ABSTRACT

The reaction product of a $C_6+$ alpha olefin/maleic anhydride copolymer with a polyfunctionalized secondary or tertiary amine has application as a heat cured coating and in cosmetic applications including hair spray as well as in inkjet ink formulations. The polyfunctionalized secondary or tertiary amine has the general formula $R_1R_2R_3N$ wherein $R_1$, $R_2$, and $R_3$ are hydrogen, alkyl, alkyl ether, hydroxyalkyl, hydroxyalkylether, aminoalkyl, aminoalkylether, or an ester of hydroxyalkyl or hydroxyalkylether containing from 1 to 15 carbon atoms; provided at least two of $R_1$, $R_2$, or $R_3$ are hydroxyalkyl, hydroxyalkylether, aminoalkyl, or aminoalkylether when the other is H; and at least one of $R_1$, $R_2$ or $R_3$ is hydroxyalkyl, hydroxyalkylether, aminoalkyl, or aminoalkylether when one is H.

19 Claims, No Drawings

REACTION PRODUCTS OF C₆+ ALPHA-OLEFIN/MALEIC ANHYDRIDE COPOLYMERS AND POLYFUNCTIONALIZED AMINES

This is a continuation-in-part application of the provisional application Ser. No. 60/070,870 filed on Jan. 9, 1998.

SPECIFICATION

Field of the Invention

The invention relates to the reaction product of a $C_6+$ olefin/maleic acid anhydride copolymer with a polyfunctionalized amine. In a preferred embodiment, the polyfunctionalized amine is a secondary or tertiary amine. The resulting product has particular applicability as a coating in inkjet ink and in cosmetic applications including hair spray and sun lotions.

BACKGROUND OF THE INVENTION

Processes for the preparation of aqueous solutions of carboxyl as well as hydroxyl-group containing copolymers have been described. See, for instance, German Patentschrift DD 247 456 A1 which discloses a method for preparation of aqueous solutions of carboxyl and hydroxyl group containing copolymers by the addition of ethylene, propylene, or alpha methyl styrene/maleic anhydride copolymers to aqueous solutions of ethanolamine or diethanolamine. These processes employ a molar ratio of amine to acid anhydride groups of one or less and produce amide derivatives with neither hydrolysis of the anhydride group nor crosslinking by conversion of the alcohol groups of the ethanolamine, or especially diethanolamine, with the anhydride occurring.

It has been now been found that aqueous solutions of carboxyl and hydroxyl group containing copolymers may be prepared from polyhydroxy functionalized tertiary amines which are incapable of forming amides. Furthermore, such products, although they may be partially crosslinked, are still water soluble. These products may be applied as coatings and, depending upon curing conditions, can yield partially to fully water impervious films.

SUMMARY OF THE INVENTION

The partially cross linked reaction product of a $C_6+$ alpha olefin and maleic anhydride copolymer with a polyfunctionalized amine has application as a heat cured coating and in cosmetic applications including hair spray and sun lotions, as well as in inkjet ink formulations.

The molar amount of polyfunctionalized amine added to the copolymer is approximately equal to the number of moles of maleic anhydride in the alpha-olefin/maleic anhydride copolymer.

The polyfunctionalized amine preferably is a secondary or tertiary amine of the general formula:

$$R_1R_2R_3N$$

wherein $R_1$, $R_2$ and $R_3$ independently are hydrogen, alkyl, alkyl ether, aminoalkyl, aminoalkylether, hydroxyalkyl, hydroxyalkylether, or an ester of hydroxyalkyl or hydroxyalkylether; provided at least two of $R_1$, $R_2$, or $R_3$ are hydroxyalkyl, hydroxyalkylether, aminoalkyl, or aminoalkylether.

DETAILED DESCRIPTION OF THE INVENTION

Reaction products of solid olefin/maleic anhydride copolymers with polyfunctionalized amines have been found to have unique applications. The resultant copolymer is an alternating copolymer of an olefinic monomer and a maleic acid anhydride with a polyfunctionalized secondary or tertiary amine.

The olefin/maleic anhydride copolymer is insoluble in water and is derived from maleic acid anhydride and a $C_6+$ alpha olefin. An alpha olefin containing up to thirty plus carbon atoms may further be employed. In a preferred embodiment, the alpha olefin for use in the invention is a $C_6–C_{24}$ alpha olefin. Most desirable results are obtained with $C_8–C_{18}$ alpha olefins. The olefin/maleic anhydride copolymer may be referred to as a poly (alkylethylenesuccinic anhydride). The copolymer exhibits hydrophilic properties (from maleic anhydride) and lipophilic properties (from the alpha-olefin).

Such copolymers are prepared by reacting the alpha olefin and maleic anhydride in approximately equimolar ratios in a solvent, in which both comonomers are soluble, such as xylene, methyl ethyl ketone, or methyl isobutyl ketone. A free radical generator, such as di-t-butyl peroxide, azobis (4-cyanovaleric acid), or salts of azobis (N,N-dimethylformamide), is employed as initiator. The reaction mixture is typically heated from about 50 to about 60° C. The number average molecular weight of the resulting copolymer is generally between about 2,000 to about 5,000. Especially desirable results are obtained where the copolymer, having a number average molecular weight about 3,000 (measured by gel permeation chromatography), is derived from a $C_8$ alpha olefin and maleic anhydride. Following completion of the polymerization, the solvent is removed by vacuum distillation. Such copolymers include those from Baker-Petrolite Polymers Division under the trademark POMAREZ™.

The polyfunctionalized amine is preferably a secondary or tertiary amine that contains at least two reactive functional groups for reaction with the alpha olefin/maleic anhydride copolymer. Thus, where, for instance, a secondary amine comprises the polyfunctionalized amine, at least one other functional group is included in the moiety. Where the amine is a tertiary amine, the polyfunctionalized amine contains at least two other functional groups.

Suitable polyfunctionalized amines are those of the formula:

$$R_1R_2R_3N \qquad (I)$$

wherein $R_1$, $R_2$, and $R_3$ may be hydrogen, alkyl, alkyl ether, hydroxyalkyl, hydroxyalkylether aminoalkyl, aminoalkylether, or an ester of hydroxyalkyl or hydroxyalkylether containing from 1 to 15 carbon atoms, typically 1 to 6 carbon atoms; provided at least two of $R_1$, $R_2$, or $R_3$ are hydroxyalkyl, hydroxyalkylether, aminoalkyl, aminoalkylether, or at least one of $R_1$, $R_2$, or $R_3$ is hydroxyalkyl, hydroxyalkylether, aminoalkyl, or aminoalkylether when the other is —H.

Alternatively, the polyfunctionalized amine may be of the formula:

wherein $R_8$ is —H and $R_9$ is hydroxyalkyl, hydroxyalkylether, aminoalkyl, or aminoalkylether.

Preferred polyfunctionalized amines are those of the formula:

$$R_1N(R_2)R_3 \qquad (II)$$

wherein $R_1$ is alkyl, alkyl ether, hydroxyalkyl hydroxyalkylether, or an ester of hydroxyalkyl or hydroxyalkylether, $R_2$ is H, hydroxyalkyl, hydroxyalkylether when R, is alkyl, alkylether, or an ester, and $R_3$ is an aminoalkyl, aminoalkylether, hydroxyalkyl, or hydroxyalkylether.

Such amines include those of the formula:

$$R_1-NH-(CH_2)_n NH_2 \qquad (III)$$

wherein n is 1 to 6.

Especially preferred amines include those containing at least one primary amino group and one hydroxyl group or one primary amino group and one secondary amino group. Specific examples include, but are not limited to, N-methyl diethanol amine, aminoethylethanolamine, N-hydroxyethyl-1,3-propanediamine, N-methyl-1,3-propanediamine, N-ethyl diethanolamine, N-butyldiethanolamine, N,N-dihydroxyethylenediamine, 2-hydroxylpropyldiethanolamine, N-hydroxyethylpiperazine, aminoethylpiperazine, alkylethylene diamines, N-propylethylenediamine, N-isopropylethylenediame, and triethanolamine. In a most preferred embodiment, the diamine is aminoethylethanolamine.

The polyfunctionalized amine most desirably contains at least two reactive functional groups—most preferably one hydroxyl group and one amino group or two amino groups—for each equivalent of maleic anhydride in the copolymer. In this fashion, one of the —COO groups of the maleic anhydride moiety may be converted to a half amide (where the reactive functional group is an amine) or half ester (where the reactive functional group is an alcohol). The second —COO group of the maleic anhydride moiety remains as a free carboxylic acid group and forms an inner salt with the remaining amine moiety of the functionalized amine.

While not intending to be bound by any theory, it is believed that in the presence of water, the polyfunctionalized secondary or tertiary amine opens the anhydride ring on the alpha olefin/maleic anhydride copolymer by reaction of the more reactive primary amine with the maleic anhydride to form an amide simultaneously forming a carboxylic acid. Reaction of a —OH containing functional group with the maleic anhydride forms an ester and a carboxylic acid. The remaining secondary or tertiary amine groups form an inner salt of the carboxylic acid resulting in an aqueous solution of a half amide (or half ester) carboxylic acid inner salt containing free —OH or >NH groups. Coatings of these solutions, upon drying, cure by the elimination of water between the carboxylic acid and —OH or >NH function forming, respectively, ester or amide crosslinks.

It is further possible to use a monofunctionalized amine as the amine compound. Such compounds include, for instance, monoethanolamine. The monofunctional amine preferentially reacts with the maleic anhydride to form amide and free carboxylic acid. It is further necessary, however, to also include a base, such as another mole of the same amine or a trialkylamine in order to neutralize the carboxylic acid. Trialkylamines of the formula $R_4R_5R_6N$ wherein $R_4$, $R_5$, and $R_6$ are independently selected from a $C_1$–$C_8$ alkyl preferably a $C_1$–$C_3$ alkyl group are especially preferred. Especially preferred tertiary amines include triethyl amine and trimethyl amine. This is a less preferred mode of operation, however, since during curing, the trialkylamine is released to the atmosphere resulting in economic loss, air pollution, and health concerns.

The alpha olefin/maleic anhydride copolymer is a solid copolymer. Especially desirable results are achieved when the copolymer is in the form of flakes, pastilles, or pellets. The pH, at the start of the reaction of alpha olefin/maleic anhydride copolymer and polyfunctionalized amine, is typically greater than or equal to 11.0. The reaction is permitted to proceed until the pH of the reaction mixture is less than or equal to 7.0. Because the reaction is somewhat exothermic, it may be necessary to cool the reaction vessel during the initial stages, but typically the temperature for reaction of those copolymers derived from a $C_6$–$C_{10}$ alpha olefin must rise to between 50 and about 60° C. to complete the reaction. As the number of carbon atoms in the alpha olefin increases, the exotherm decreases and cooling is often necessary. For instance, when the alpha olefin is a $C_{14}$–$C_{18}$, the reaction is run at room temperature throughout the duration.

An indication of the completion of the reaction rests in the solubility of the final product. While the alpha olefin/maleic anhydride copolymer is insoluble in water, the reaction product is soluble in water. Thus, the reaction may be terminated upon dissolution of the alpha olefin/maleic anhydride copolymer. At room temperature, the final product is an aqueous solution.

The molar ratio of amine to maleic anhydride in the alpha olefin/maleic anhydride copolymer is generally about 1:1. It is possible to use somewhat less than one mole of diamine per mole of contained anhydride. However, if too little functionalized amine is used, insufficient reaction occurs to yield a soluble product. Where the amine is a functionalized secondary or tertiary amine of formula (I) above and if the temperature is raised in order to attain a further degree of reaction, a significant amount of secondary amine and/or hydroxyl (if present) will react with the remaining anhydride to give cross linked products which form gels. In such cases, adding aqueous base, such as sodium hydroxide, may break the gel structure and give a clear solution. However, such products fail to cure fully when coated and dried. Thus, they give coatings that allow some penetration of water.

The product formed is an aqueous solution, typically containing from about 20 to about 40 percent solids. The viscosity of the product may be as high as 2000 cPs at 25° C. Higher viscosities are indicative of excessive cross linking. The major product of the reaction is an inner salt resulting from the opening of the anhydride ring by attack of the primary amino group to give an amidocarboxylic acid. It is also possible that some amount of a disubstituted amidocarboxylic acid is formed due to opening of the anhydride ring by the secondary amine and, in the case where R contains a hydroxyl group, some ester may be formed.

The number average molecular weight of the resulting copolymer is between about 2,000 to about 5,000, preferably from about 2,500 to about 3,500.

The solutions are coated onto a substrate and then heat cured to drive off the moisture. Where the reaction product is formed from a monofunctionalized amine (such as monoethanolamine), ester crosslinks are formed while losing the volatile tertiary amine. As a result, a water impervious coating results.

Where the reaction product is formed from a polyfunctionalized secondary or tertiary amine, the amine is incorporated into the formed product. The crosslink forms from reaction of either the secondary amino group or a hydroxyl group with carboxylic acid inner salt. Thus, no volatile amine is lost in the process. It is unnecessary to perform a heat curing stage where the reaction product is formed from a polyfunctionalized secondary amine. The referenced crosslinks will form over time.

While it is possible to use more than one mole of functionalized amine per mole of contained anhydride, too many carboxyl functions will react with the excess amine upon curing if too great an excess of amine is used. This will result in water-permeable coatings attributable to insufficient cross linking and increased hydrophilicity of the product on account of the excessive number of amino groups.

Acceptability of use of the resulting product to serve as a water resistant coating is dependent on the ability of the reaction product, when applied as an aqueous solution, to coalesce into a film after the water evaporates. Evaporation of water may be enhanced either by adding a lower alcohol (generally a $C_1$–$C_6$ alcohol, such as methanol, ethanol, propanol, isopropanol, n-butanol, sec-butyl alcohol, and iso-butyl alcohol) to the solution before applying it to the substrate or by providing heat to the substrate after applying the solution. Alternatively, a combination of the two methods may be used.

The resulting films resist penetration of water. The extent of water resistivity is dependent on the temperature the resultant film is subjected to as well as the amount of time that passes after film formation before the film is tested for water resistance. While not desiring to be bound by any particular theory, it is believed that water resistance of the film is attained by reaction of the carboxyl groups of the inner salt with either the secondary amino groups or the hydroxyl groups (if present) resulting in the release of water and the formation of a cross linked higher molecular weight polymer.

The reaction product further has applicability in inkjet ink formulations in light of its smear resistance properties. In addition, it has applicability in adhesives and paints. The invention has particular applicability in the production of creams (such as sunscreen).

Thermal ink jet printing compositions typically contain a dye, a liquid medium containing water, and a surfactant. See, for instance, U.S. Pat. Nos. 5,019,166 and 4,783,220. The products described herein may be employed in inkjet ink formulations as a surfactant and can be thereafter cured to improve waterfastness of the ink to prevent feathering on plain paper. Representative formulations of compositions for thermal inkjet inks are:

Dye Composition A
  Reaction product of $C_6$+ alpha olefin/maleic anhydride and functionalized secondary or tertiary amine: 1.0 to 25 wt. %
  Dye: 1 to about 100% dye; and
  Water: Balance.

Dye Composition B
  Reaction product of $C_6$+ alpha olefin/maleic anhydride and functionalized secondary or tertiary amine: 0.5 to 15 wt. %;
  Dye: 8 to 10 wt. %;
  ethylene glycol: 10 to 20 wt. %;
  Water: Balance.

Further, the reaction product finds application in the personal care area such as in low-volatile organic hair spray formulations where the originally water-soluble polymer will cure to a resinous film having resistance to water. Traditionally, hair sprays consist of a resinous polymer dissolved or suspended in a volatile solvent that, upon evaporation of the solvent, leaves a film of the resin on the hair. Recent legislation requires that hair sprays contain no more than 80% volatile organic compounds (VOC). In 1998, the allowable VOC content will be lowered to a 55% maximum. Thus, the ultimate aim of the industry is to reduce VOC content as much as possible. However, a major problem being encountered in reducing VOC much below 80% is that more hydrophilic resins must be used and these resins either do not provide sufficient "hold" or are too hygroscopic and become tacky, especially in high humidity environments. The present invention provides a solution to such shortcomings. At the same time, it eliminates the release of volatile tertiary amines with their attendant problems.

A typical hair spray contains basically about 95% ethanol and 5% resin. The most commonly used resins were copolymers of maleic anhydride and methyl vinyl ether. As the VOC content was lowered to 80%, variations on these copolymers to make them more compatible with the more hydrous system are used. Also, other resins, such as polyacrylates, polyacrylamides, and copolymers of these may also be used. In addition, small amounts (<1% total) of conditioners, compatibilizers, and vitamins are often added. The same trend is generally true for the proposed 55% VOC hair sprays as well; more hydrophilic resins and additional compatibilizers and conditioners. The products of this invention would be used in place of some or all of the resin in a hair spray.

The reaction product further has utility in preparation of sun lotions.

The following examples will illustrate the practice of the present invention in its preferred embodiments. Other embodiments within the scope of the claims herein will be apparent to one skilled in the art from consideration of the specification and practice of the invention as disclosed herein. It is intended that the specification, together with the examples, be considered exemplary only, with the scope and spirit of the invention being indicated by the claims which follow.

EXAMPLES

All percentages expressed herein are percent by weight.

Example 1

In a 250 ml. beaker with magnetic stirrer were added 82.0 g of deionized water and 9.4 g (0.009 mole) of aminoethylethanolamine, a product of Union Carbide Company. The beaker was placed into an ice water bath and stirred until cool. While maintaining the beaker at a temperature of 50° C., 27.6 g (0.10 mole) of pastilles of $C_{14}$ alpha olefin/maleic anhydride copolymer was added over five minutes. The temperature was then maintained between 5 to about 10° C. for about 2.5 hours. It was then allowed to warm to room temperature. The beaker was maintained at room temperature for about 2 hours. The pH of the mixture in the beaker was approximately 8.0. About 10% NaOH(5.0 g, 0.0125 mole) was then added. This raised the pH to about 8.7. The mixture was then left to stir overnight. Some pastilles remained undissolved. The pH of the mixture was then about 8.5. The solution was then heated for about 1.5 hours at about 65 to about 70° C. It was then cooled and adjusted to about 30% solids concentration (about 9.0 pH). The solution was then drawn down on a Lenetta card. It rendered a glossy film. Three days later, drops of water were then placed on the card. Slight beading was exhibited. After evaporation of the water, there was observed some penetration of the coating. The card was then cured in a 120° C.

oven for about 10 minutes. After one hour, a large drop of water was then placed on the card. Some beading was observed. The next day, some penetration of coating was observed. A drop of water was then placed on the card. Beading (at an angle less than 90° was observed. After drying, some penetration of coating was observed.

Example 2

In a 250 ml. beaker with magnetic stirrer were added 86.0 g of deionized water and 9.4 g (0.09 mole) of aminoethylethanolamine. The beaker was maintained at a temperature of between about 31 to about 37° C. while being stirred. Over a ten minute period was added about 27.6 g (0.10 mole) of pastilles of $C_{14}$ alpha olefin/maleic anhydride copolymer. After stirring for about 5 hours at room temperature to about 37° C., there was noted some undissolved pastilles. The pH of the solution was about 7.9. The solution was continuously stirred overnight. The next day, the pH of the solution was 7.8. The solution was very thick with still some undissolved pastilles. The mixture was heated to about 65 to about 70° C. for about one hour while stirring. The mixture became overly thick to stir with the magnetic bar. The mixture was cooled and the solids adjusted to about 30%. The resulting solution, having a pH of about 8.0, was clear. A draw down was made on a Lenetta card. It rendered a glossy film. The viscosity of the product was about 800 cP (LVT #3 at 3 rpm). Three days later, drops of water were placed on the card. Some beading was exhibited. After evaporation of the water, there was observed some penetration of the coating. The card was then cured in a 120° C. oven for about 10 minutes. After one hour a large drop of water was then placed on the card. Beading was observed. The next day, some penetration of coating was observed. A drop of water was then placed on the card. Beading at an angle less than 90° was observed. After drying, slow (but significant amount of) penetration of coating was observed. This suggests the use of the substance as a controlled release of fertilizer and pesticides.

Example 3

To a 250 ml. beaker with a magnetic stirrer was added 89.0 g of deionized water and 10.4 g (0.10 moles) of aminoethylethanolamine. The beaker was stirred with a mechanical stirrer. To the beaker was added 27.6 g (0.10 mole) pastilles of $C_{14}$ alpha olefin/maleic anhydride copolymer over a period of five minutes at 16° to 18° C. Allowed to warm to room temperature and left stirring for 7 hours. After leaving overnight, water was added to adjust solids to 30% giving a clear solution having a pH of 8.5. The solution was then drawn down on a Lenetta card. The next day, a drop of water was placed on the card. After evaporation of the water, significant penetration of the coating was evident. The card was left overnight in a 120° C. oven. It was then allowed to cool for 2 hours before placing a drop of water on it. The water had a very high contact angle and evaporated without a trace indicating no penetration of the coating.

Example 4

The procedure of EXAMPLE 3 was followed, except 9.2 g. (0.088 mole) of aminoethylethanolamine and 28.9 g (0.088 mole) of pastilles of C18 alpha olefin/maleic anhydride copolymer were used. A slightly hazy solution (30% solids) was obtained having a pH of 8.7 and viscosity of 25 cP.

Example 5

To a 100 ml. beaker with a magnetic stir bar was added 18.7 g of deionized water and 3.0 g (0.02 mole) of triethanolamine. The solution was stirred with a magnetic stirrer and pastilles of C8 alpha olefin/maleic anhydride copolymer (5.0 g, 0.025 mole) were added. The beaker was covered with a watch glass and left to stir at 40–45° C. After 20 hours, complete solution was obtained (23.5 g net weight corresponding to 34% solids) having a pH of 5.8.

Example 6

In a similar manner to EXAMPLE 5, C14 alpha olefin/maleic anhydride copolymer (7.6 g, 0.0275 mole) was reacted with triethanolamine (3.3 g, 0.022 mole) in 25.4 g of deionized water. In this case, no heat was applied and the mixture simply stirred at room temperature for 24 hours resulting in a solution (33 g net weight corresponding to 33% solids) having a pH of 6.6.

Example 7

By the procedure of EXAMPLE 6, C18 alpha olefin/maleic anhydride copolymer (22.0 g, 0.067 mole) was reacted with triethanolamine (8.0 g, 0.053 mole) in 70 g of deionized water. The resulting solution was adjusted to 30% solids content by adding deionized water and had a pH of 6.8 and a viscosity of 250 cP.

Example 8

An aliquot of product from EXAMPLE 7 was diluted with deionized water to 5% solids and a trace amount of zinc oxide added. Two circles of S&S filter paper (#597) were immersed in this solution for about 1 minute then left overnight to air dry. Each circle, as well as a circle of untreated #597 filter paper, was cut in half. With McCormick blue food coloring, the word "Blue" was printed on each of the six pieces of paper. After two hours, coated papers were cured in a 120° C. oven for 0, 0.5, 2.0 and 5.0 minutes. The untreated papers were cured at 120° C. for 0 and 5.0 minutes. After a further 2 hours, each paper was held under running water until no more dye washed out. Upon drying, the following observations were made:

| Sample | Cure Time @ 120° C. | Observation |
| --- | --- | --- |
| Blank | 0 min. | Pink color remains |
| Blank | 5.0 min. | Pink/Purple color |
| Product EX 7 | 0 min. | Pink/Purple color |
| Product EX 7 | 0.5 min. | Faded Blue color |
| Product EX 7 | 2.0 min. | Blue color |
| Product EX 7 | 5.0 min. | Strong Blue color |

Example 9

To approximately 5 g of each of four McCormick food color solutions (blue, green, red and yellow) was added 0.5 g of the product, from EXAMPLE 4. Printing with each solution or "ink" using a stylus was applied to plain paper (A) and to ink jet paper, HP-51630Y (B). Similarly, printing on both types of paper was done using the four food coloring solutions without any additive. With the ink jet paper, both "inks" absorbed much more readily than with the plain paper. With the plain paper, the untreated "ink" resulted in excessive feathering which was not observed with the treated "ink". After air drying for about 1 hour, each sheet was cut in half so that each half contained printing with each color. One half of each sheet was then soaked for 1 minute in 500 ml of tap water, rinsed briefly under running water, then left to air dry. The following observations of the water-washed half sheets were made (compared to the same half sheet that was not washed):

| Paper | Treated Ink | Untreated Ink |
|---|---|---|
| A | Blue and green washed out to a considerable extent, but red and yellow washed out very little. | All colors washed out considerably (esp. yellow). All smeared more than with treated ink. |
| B | Little wash out of any color. Some smear (esp. green and yellow). | Little wash out of any color. More smear than with treated ink in all cases. |

Example 10
Non-VOC Hairspray

| Material | % by Weight |
|---|---|
| Deionized water | 83.18 |
| Product from EX 4 | 16.67 |
| Preservative | 0.15 |

Procedure: Add the product from EXAMPLE 4 to water, then add other ingredients. If necessary, add citric acid to adjust pH to 7.0–8.0.

Example 11
Water-Proof Sunscreen Lotion

| Material | % by Weight |
|---|---|
| A | |
| Deionized water | 58.5 |
| Product from EX 4 | 15.0 |
| Propylene Glycol | 1.0 |
| B | |
| Isopropyl Myristate | 5.0 |
| Cetearyl Alcohol | 1.0 |
| Ethylene Glycol Monostearate | 1.5 |
| Mineral Oil | 4.0 |
| Benzophenone-3 | 6.0 |
| Octocrylene | 8.0 |
| C | |
| Preservative | Q.S. |

Procedure: Separately heat A and B to 75° C. Add B to A and mix until uniform. Cool to 45° C. and add C.

What is claimed is:

1. An aqueous solution comprising the reaction product of:
   (A) a $C_6+$ alpha olefin/maleic anhydride copolymer:
   (B) a polyfunctionalized secondary or tertiary amine having the general formula $R_1R_2R_3N$ wherein $R_1$, $R_2$, and $R_3$ are hydrogen, alkyl, alkyl ether, hydroxyalkyl, hydroxyalkylether, aminoalkyl, aminoalkylether, or an ester of hydroxyalkyl or hydroxyalkylether; provided at least two of $R_1$, $R_2$, or $R_3$ are hydroxyalkyl, hydroxyalkylether, aminoalkyl, or aminoalkylether; or at least one of $R_1$, $R_2$, or $R_3$ are hydroxyalkyl, hydroxyalkylether, aminoalkyl, or aminoalkylether when the other is H in water; wherein the molar ratio of polyfunctionalized amine to the maleic anhydride in the copolymer is about 1:1.

2. The aqueous solution of claim 1, wherein the number average molecular weight of the $C_6+$ alpha olefin/maleic anhydride copolymer is between about 2,000 to about 5,000.

3. The aqueous solution of claim 1, wherein the number average molecular weight of the $C_6+$ alpha olefin/maleic anhydride copolymer is from about 2,500 to about 3,500.

4. The aqueous solution of claim 1, wherein the product contains from about 20 to about 30 weight percent solids.

5. The aqueous solution of claim 1, wherein the product has a viscosity of no more than 300 cP at 25° C.

6. The aqueous solution of claim 1, wherein the alpha-olefin is a $C_6$–$C_{18}$ alpha olefin.

7. The aqueous solution of claim 1, wherein the polyfunctionalized secondary or tertiary amine is of the formula:

$$R_1N(R_2)R_3 \qquad (II)$$

wherein $R_1$ is alkyl, alkyl ether, hydroxyalkyl, hydroxyalkylether, or an ester of hydroxyalkyl or hydroxyalkylether, $R_2$ is H, hydroxyalkyl, or hydroxyalkylether when $R_1$ is alkyl, alkylether, or ester.

8. The aqueous solution of claim 7, wherein the polyfunctionalized secondary or tertiary amine is selected from N-methyl diethanol amine, aminoethylethanolamine, N-hydroxyethyl-1,3-propanediamine, N-methyl-1,3-propanediamine, N-ethyl diethanolamine, N-butyldiethanolamine, N, N-dihydroxyethylenediamine, 2-hydroxylpropyldiethanolamine, N-hydroxyethylpiperazine, aminoethyl piperazine, alkylethylene diamines, N-propylethylenediamine, N-isopropylethylenediamine, and triethanolamine.

9. The aqueous solution of claim 7, wherein the polyfunctionalized secondary or tertiary amine is aminoethylethanolamine.

10. The aqueous solution of claim 7, wherein the polyfunctionalized secondary or tertiary amine is triethanolamine.

11. A heat cured coating comprising the aqueous solution of claim 1.

12. An inkjet ink formulation comprising the aqueous solution of claim 1.

13. A hair spray comprising the aqueous solution of claim 1.

14. A sun lotion comprising the aqueous solution of claim 1.

15. A process of preparing an aqueous solution of a partially crosslinked functionalized polymer containing from about 20 to about 30 weight percent solids and having a viscosity of no more than about 300 cP at 25° C. which comprises reacting in water
   (A) a $C_6+$ olefinic/maleic anhydride copolymer;
   (B) a polyfunctionalized secondary or tertiary amine of the general formula $R_1R_2R_3N$ wherein $R_1$, $R_2$, and $R_3$ are independently selected from hydrogen, alkyl, alkyl ether, hydroxyalkyl, hydroxyalkylether aminoalkyl, aminoalkylether, or an ester of hydroxyalkyl or hydroxyalkylether provided at least two of $R_1$, $R_2$, or $R_3$ are hydroxyalkyl, hydroxyalkylether, aminoalkyl, or aminoalkylether; or at least one of $R_1$, $R_2$, or $R_3$ is hydroxyalkyl, hydroxyalkylether, aminoalkyl, or aminoalkylether when the other is H.

16. The process of claim 15, wherein the molar amount of polyfunctionalized secondary or tertiary amine reacted with the copolymer is approximately equal to the molar amount of maleic anhydride in the copolymer.

17. The process of claim 15, wherein the olefinic monomer is of the formula:

where R is a hydrocarbon group such as an alkyl group, $(CH_2)_nH$, where n is a number from 4 to 50.

18. The process of claim 15, wherein the polyfunctionalized secondary or tertiary amine is of the formula R—NH—$(CH_2)_nNH_2$.

19. The process of claim 18, wherein the diamine is aminoethylethanolamine, N-hydroxy-ethyl-1,3-propanediamine, N-methyl-1,3-propanediamine, aminoethylpiperazine, N-propylethylenediamine, or N-isopropylethylenediame.

* * * * *